United States Patent [19]
Giertz et al.

[11] Patent Number: 4,906,614
[45] Date of Patent: Mar. 6, 1990

[54] METHOD OF TREATING POSTTRAUMATIC NERVOUS INJURIES WITH DIPEPTIDE DERIVATIVES

[75] Inventors: Hubert Giertz, Aachen-Orsbach; Hans Barth, Aachen; Leopold Flohe, Roetgen, all of Fed. Rep. of Germany

[73] Assignee: Gruenenthal GmbH, Stolberg, Fed. Rep. of Germany

[21] Appl. No.: 207,115

[22] Filed: Jun. 14, 1988

Related U.S. Application Data

[63] Continuation of Ser. No. 102,438, Sep. 29, 1987, abandoned, which is a continuation of Ser. No. 819,056, Jan. 15, 1986, abandoned.

[30] Foreign Application Priority Data

Jan. 23, 1985 [DE] Fed. Rep. of Germany ....... 3502041

[51] Int. Cl.$^4$ .............................................. A61K 37/02
[52] U.S. Cl. ......................................... 514/18; 514/19
[58] Field of Search ..................................... 514/18, 19

[56] References Cited

U.S. PATENT DOCUMENTS 4,608,365 8/1986 Engel ..................................... 514/18

OTHER PUBLICATIONS

Griffiths, "Thyrotrophin Releasing Hormone: Endocrine and Central Effects", *Psychoneuroendocrinology*, vol., 10, #3, pp. 225–235 (1985).
McIntosh et al., "Beneficial Effect of the TRH Analog CG-3703 on Hypertension and Neurological Deficit Caused by Traumatic Brain Injury in Rats", *Cir. Shock*, vol. 21, p. 376 (1987).
Faden et al., Neuropeptides in Spinal Cord Injury: Comparative Experimental Models, *Peptides*, vol. 4, pp. 631–634 (1983).
Webster et al., "Antinociceptive Effects of Thyrotrophin-Releasing Hormone and Its Analogues in the Rat Periaqueductal Grey Region", *Neuroscience Letters*, vol. 42, No. 1, pp. 67–70 (1983).
Faden et al., "Thyrotropin-Releasing Hormone Improves Neurologic Recovery After Spinal Trauma in Cats", 305 *N. Eng. J. Med.*, 1063 (1981).
Faden et al., "Comparison of Thyrotropin-Releasing Hormone (TRH), Naloxone, and Dexamethasone Treatments in Experimental Spinal Injury", 83 *Neurology* 673 (1983).
Faden et al., "Opiate Antagonists and Thyrotropin-Releasing Hormone", 252 *J. Am. Med. Assn.* 1452 (1984).
Metcalf, "Regulatory Peptides as a Source of New Drugs–The Clinical Prospects for Analogues of TRH Which are Resistant to Metabolic Degradation", 4 *Brain Research Reviews* 389 (1982).
Faden, "Opiate Antagonists and Thyrotropin-Releasing Hormone", 252 *J. Am. Med. Assn.* 1177 (1984).
Faden et al., "Effects of TRH Analogs on Neurologic Recovery After Experimental Spinal Trauma", 35 *Neurology* 1331, (1985).
Hoppe et al., "Safety and Endocrinological Effects of TRH-Analog CG 3509 After Single and Multiple Administration in Normal Volunteers", *Thyrotropin-Releasing Hormone* 374 (1983).
Griffith et al., "Inactivation of Some TRH Analogues by Rat Brain: Product Indentification by HPLC", *Thyrotropin-Releasing Hormone*, 368 (1983).
Benkert et al., "Clinical and Endocrinological Effects of the TRH Analogue CG 3509 in Depression", *Thyrotropin-Releasing Hormone* 353 (1983).
Flohe et al., "Biological Effects of Degradation-Stabilized TRH Analogues", *Thyrotropin-Releasing Hormone* 327 (1983).
Metcalf, "The Neuropharmacology of TRH Analogues", *Thyrotropin-Releasing Hormone* 315 (1983).
Heal et al., "Actions of TRH and its Analogues on the Mesolimbic Dopamine System", *Thyrotropin-Releasing Hormone* 271 (1983).

(List continued on next page.)

*Primary Examiner*—Delbert R. Phillips
*Attorney, Agent, or Firm*—Foley & Lardner, Schwartz, Jeffery, Schwaab, Mack, Blumenthal & Evans

[57] ABSTRACT

A method of preventing or treating posttraumatic nervous injuries by administering a compound of the formula:

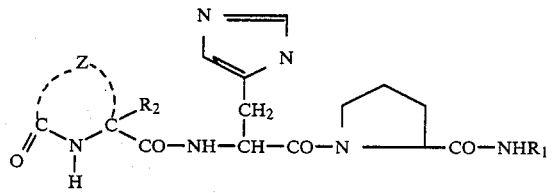

wherein $R_1$ is hydrogen, a lower alkyl group, cyclohexyl or benzyl; Z is one of the groups

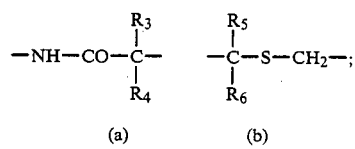

(a)                (b)

if Z is a group (a), $R_2$ and $R_3$ together represent an additional bond between the carbon atoms bearing them, or if Z represents a group (b), $R_2$ is hydrogen; $R_4$ is hydrogen or lower alkyl; $R_5$ is hydrogen, lower alkyl or phenyl, and $R_6$ is hydrogen or methyl. Hydrates or pharmaceutically acceptable acid addition salts may also be used in the method. Pharmaceutical compositions used in this method containing such compounds in a prophylactically or therapeutically effective amount may be administered by infusion, injection, orally, perorally, rectally, percutaneously or other route.

12 Claims, No Drawings

OTHER PUBLICATIONS

Bennett et al., "TRH and Catecholamine Neurotransmitter Release in the Central Nervous System", *Thyrotropin-Releasing Hormone* 253 (1983).

Webster et al., "Induction of Wet-Dog Shaking in Rats by Analogues and Metabolites of Thyrotropin-Releasing Hormone (TRH)", 5 *Regulatory Peptides* 43 (1982).

Bennett et al., "Analeptic Effect of Intracerebral Injection of TRH and Stabilized Analogues in the Pentobarbitone-Anaesthetized Rat", *Proceedings of the British Pharmacological Society* (1982).

Heal et al., "Behavioral Effects of Central and Peripheral Injection of Various Analogues and Metabolites of Thyrotropin Releasing Hormone (TRH)", 20 *Neuropharmacology* 947 (1981).

Friderichs et al., "Activity of Thyroliberin Analogs with a Modified Pyroglutamyl Residue on the Central Nervous System", *Structure and Activity of Natural Peptides* 462 (1981).

Schwertner et al., "Synthesis of Thyroliberin Analogs with Modified Pyroglutamyl Residues", *Structure and Activity of Natural Peptides* 397 (1981).

Friderichs et al., "Activity of Thyroliberin Analogs with a Modified Pyroglutamyl Residue on the Central Nervous System", 360 *Z. Physiol. Chem.* 1146 (1979).

Schwertner et al., "Synthesis of Thyroliberin Analogs with Modified Pyroglutamyl Residues", 360 *Z. Physiol. Chem.* 1195 (1979).

Yehuda et al., "Effects of TRH and PS-24 on Colonic Temperature and Motor Activity of Rats: Possible Role of Dopamine", *Peptides*, vol. 2, pp. 131-135 (1981).

"CG 3703", *Drugs of the Future*, vol. 8, No. 12, pp. 1007-1009 (1981).

Hennies et al., "Effects of the Thyroliberin Analogue CG 3703 on Noradrenergic and Serotoninergic Transmission in Rodents", *Biochemical Pharmacology*, vol. 31, No. 14, pp. 2430-2432 (1982).

Dettmar et al., "Can Biological Stability Account for the Enhanced CNS Potency of All TRH Analogues?", *Thyrotropin-Releasing Hormone* 361 (1983).

Griffiths et al., "Mechanisms of Brain Inactivation of Centrally-Acting Thyrotropin-Releasing Hormone (TRH) Analogues", 5 *Regulatory Peptides* 1-11 (1982).

Bauer, "Thyroliberin Analogues as Competitive Inhibitors of Thyroliberin Degradation by Brain Enzymes", *Z. Physiol. Chem.* vol. 360, 1126 (1979).

Hennies et al., "Norepinephrine and Serotonin Turnover in Rodents After Application of the TRH Analogue CG 3703", *Thyrotropin-Releasing Hormone* 371 (1983).

Stezowski et al., "Conformational Properties of TRH and TRH Analogs as Determined by Single Crystal X-Ray Diffraction Techniques", *Thyrotropin-Releasing Hormone* 385 (1983).

Bauer et al., "Degradation of TRF and TRF Analogues by Brain and Serum Enzymes", *Structure and Activity of Natural Peptides* 437-47 (1981).

Fukuda et al., "Behavioral and EEG Alterations with Brain Stem Compression and Effect of Thyrotropin Releasing Hormone (TRH) in Chronic Cats", *Folia Pharmacol.*, vol. 75, No. 4, pp. 321-331 (1979).

METHOD OF TREATING POSTTRAUMATIC NERVOUS INJURIES WITH DIPEPTIDE DERIVATIVES

This application is a continuation of application Ser. No. 102,438, filed Sept. 29, 1987, which in turn is a continuation of Ser. No. 819,056, filed Jan. 15, 1986. now abandoned.

BACKGROUND OF THE INVENTION

Injuries of the spinal cord and/or brain occur relatively often in traffic or sports accidents. Depending on the degree or severity of these traumata, more or less pronounced symptoms develop (such as paraplegia or paralysis due to spinal cord injuries or central paralysis, impairment of the memory and other neurological deficiencies due to traumata of the brain) which often are irreversible and in any case are difficult to cure. Faden et al., in *New England Journal of Medicine*, Vol. 305, No. 18, pp. 1063–67, reported that thyrotropin-=releasing-hormone (TRH=L-pyroglutamyl-L-histidyl-L-prolinamide) significantly improves recovery of the motoric function after experimental spinal cored injury in animal experiments when treatment occurs during the first 24 hours following the trauma. Fukuda et al., in *Nippon Yakurigaku Zasshi*, Vol. 75, No. 4, pp. 321∝31 observed a dose-dependent positive effect of TRH in animal experiments on EEG alterations resulting from traumata of the brain caused by brain stem compression in cats. Takahashi et al., U.S. Pat. No. 4,059,692, teaches that impaired consciousness in humans due to functional or organic damage of the brain, such as cranial trauma, cerebrovascular disorder, cerebral surgery or brain tumor, may be improved by administration of TRH successively for at least 10 days.

Unfortunately, in living organisms TRH is quickly metabolized and inactivated by enzymatic cleavage of the pyroglutamyl group and/or deamidation. Accordingly, TRH or a salt thereof is generally administered by continuous intravenous infusions in high doses, and only in exceptional cases is intramuscular or peroral administration considered.

Attempts have been made to synthesize, by chemical modification of the TRH-molecule, compounds which have the desired biological activities of TRH but which are stable against the metabolizing and inactivating enzymes and which thus avoid the disadvantages of TRH resulting from its instability. See: Metcalf, "The Neuropharmacology of TRH Analogues," *Thyrotropin-Releasing Hormone:* Griffiths et al, eds.; Raven Press, New York, (1983). These TRH-modifications show, however, different profiles of biological activity, and, in particular, their activities are only partially equivalent to those of TRH. These results were ascertained, however, only with respect to the endocrinological effects and to the stimulating effects on the central nervous system. Accordingly it is completely unknown and unpredictable whether such TRH-modifications have any effects - and, if so, which effects they may have - on posttraumatic nervous injuries, especially on paraplegia due to spinal cord injuries and/or on neurological deficiencies after traumata of the brain.

compounds corresponding to the formula I:

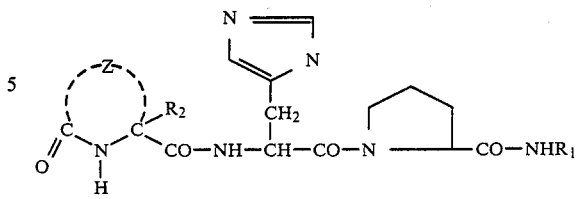

wherein $R_1$ represents a hydrogen atom, an alkyl group containing one to six carbon atoms, a cyclohexyl group or a benzyl group, Z is one of the following groups (attached to the CO-group in the ring by the valence marked with an asterisk):

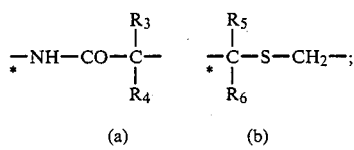

if Z represents a group (a), $R_2$ and $R_3$ represent an additional bond between the carbon atoms to which $R_2$ and $R_3$ are attached, or if Z represents a group (b), $R_2$ is a hydrogen atom, $R_4$ and $R_5$ are the same or different and each represents hydrogen or an alkyl group containing one to three carbon atoms and wherein $R_5$ also may represent a phenyl group and $R_6$ represents a hydrogen atom or a methyl group. The compounds of formula I (as well as hydrates and acid addition salts thereof,) and their preparation have been described e.g., by Schwertner et al. in "Structure and Activity of Natural Peptides'" (Editors W. Voelter and G. Weitzel), Walter de Gruyter-Verlag, Berlin - New York, 1981, pp. 397–415, in U.S. Pat. No. 4,045,556, in British Pat. No. 1,564,078, the disclosures of which are incorporated herein by reference, and elsewhere.

The aforementioned publications disclose that the compounds of formula I on parenteral or oral administration provide long lasting central nervous system stimulating effects and that the toxicity of the compounds is very low. Due to these pharmacological properties, the compounds of formula I according to the publications mentioned above and further references can be used as psycho-stimulating agents or as antidepressive agents. Accordingly the known fields of application for the compounds of formula I relate only to chronic metal illness and not to acutely occurring neurological injuries. It was unforeseeable that the compounds of formula I or medicaments containing them could be used for treatment of posttraumatic nervous injuries, especially to prevent or to treat paraplegia due to spinal cord injuries and/or neurological deficiencies after traumata of the brain.

SUMMARY OF THE INVENTION

It is the object of the present invention to provide a method of preventing or treating of post-traumatic nervous injuries.

It is also an object of the invention to provide a method especially suitable for preventing or treating paraplegia or paralysis due to spinal cord injuries and/or neurological deficiencies after traumata of the brain.

Another object of the invention is to provide pharmaceutical compositions for use in the method of preventing or treating posttraumatic nervous injuries.

A further object of the invention is to provide a method of treating posttraumatic nervous injuries which is especially suitably for early use or administration at the site of an accident.

Yet another object of the invention is to provide a method of prophylaxis or therapy of posttraumatic nervous injuries caused by accidents, such as paraplegia and/or neurological deficiencies.

These and other objects of the invention are achieved by providing a method comprising administering to a patient suffering from traumata of the spinal cord or of the brain an effective nervous injury affecting amount of a compound corresponding to the formula I:

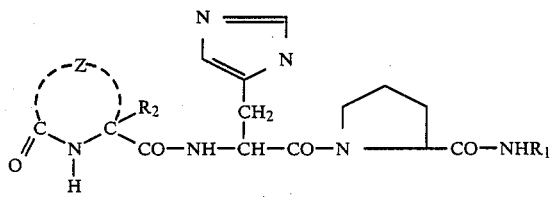

wherein
$R_1$ represents a hydrogen atom, an alkyl group containing one to six carbon atoms, a cyclohexyl group or a benzyl group, Z is one of the following groups in which the valence marked with an asterisk (*) is attached to the ring carbonyl group in formula I:

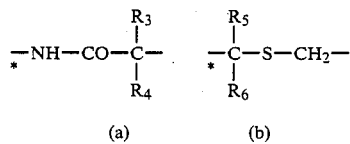

(a)                    (b)

If Z represents a group (a), $R_2$ and $R_3$ together represent an additional bond between the carbon atoms to which they are attached, or if Z represents a group (b), $R_2$ represents a hydrogen atom, $R_4$ and $R_5$ are the same or different and each represents hydrogen or an alkyl group containing one to three carbon atoms, or $R_5$ also may represent a phenyl group, and $R_6$ represents hydrogen or a methyl group, in hydrated or unhydrated form or a pharmaceutically acceptable salt of such a compound with an acid.

It now surprisingly has been found that the symptoms due to traumata of the spinal cord and/or of the brain can be prevented or treated successfully, by administration of a compound formula I in anhydrous or hydrated form or an acid addition salt thereof with a pharmaceutically acceptable acid.

The manner in which the compound of formula I is administered as well as the amount of this compound which is therapeutically or prophylactically effective in any specific patient being treated may vary somewhat depending on the degree of the injuries in the individual patient, and may be determined in each individual case by the treating physician in accordance with generally accepted principles governing administration of pharmaceutical compositions.

The compounds of formula I as well as their hydrates and salts are relatively stable products. Thus, their incorporation into pharmaceutical compositions in the form and amount desired poses no problems or difficulties for an ordinarily skilled pharmacist.

DETAILED DESCRIPTION OF PREFERRED EMBODIMENTS

In general, all compounds of formula I, their hydrates and their pharmaceutically acceptable salts with acids are suitable for use in the method of the invention for preventing or treating posttraumatic nervous injuries, especially in the prevention or treatment of paraplegia or paralysis due to spinal cord injuries and/or of neurological deficiencies after traumata of the brain. Suitable compounds within the scope of the invention include, for example:

orotyl-L-histidyl-Lproline-(N-methylamide);
orthyl-L-hsitidyl-L-proline-(n-n-butylamide);
orthyl-L-histidyl-L-proline-(n-benzylamide);
5-ethylorotyl-L-histidy-L-prolinamide;
5-n-propylorotyl-L-histidyl-L-prolinamide;
5-oxo-thiomorpholine-3(L)-carbonyl-Lhistidyl-L-prolinamide;
5-oxo-6-methyl-thiomorpholine-3(L)-carbonyl-L-histidyl-L-proline-(N-methylamide);
5-oxo-6-phenyl-thiomorpholine-3(L)-carbonyl-L-hsitidyl-L-prolinamide;
5-oxo-6-ethyl-thiomorpholine-3(L)-caronlyl-L-histidyl-L-prolinamide;
5-oxo-6-(n-propyl)-thiomorpholine-3(L)-carbony-L-histidyl-L-prolinamide;
5-oxo-6, 6-dimethyl-thiomorpholine-3(L)-carbonyl-L-histidyl-L-prolinamide;

and other similar compounds within the scope of formula I.

Preferred compounds of formula I are those of the formulae Ia and Ib:

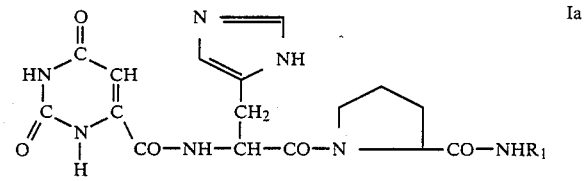

and

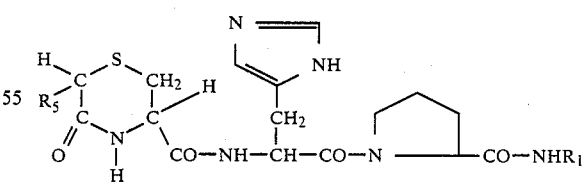

wherein $R_1$ and $R_5$ have the same meanings as above. Preferably, $R_1$ in formulas I, Ia and Ib represents a hydrogen atom.

Especially preferred compounds of formula I include orotyl-L-histidyl-L-prolinamide and 5-oxo-6-methyl-thiomorpholine-3(L)-carboinyl-L-histindyl-L-prolinamide, their hydrates and acid addition salts.

As used herein the term "acid addition salts" refers to pharmaceutically acceptable salts of compounds of formula I in anhydrous or hydrated form with acids. Useful acid addition salts include, for example, tartrates, maleates, citrates, hydrochlorides, hydrobromides, phosphates, sulfates, formates, acetates, benzoates, salicylates, benzenesulfonates and other equivalent salts.

Patents treatable by the method of the invention include, for example, both large and small mammals.

The manner in which the compound of formula I is administered to the patient suffering from trauma of the spinal cord and/or of the brain to prevent or to treat posttraumatic nervous injuries depends in principle on the degree of the trauma in the individual patient. For instance, in case of victims of an accident, if possible the first dose of the medicament containing a compound of formula I should be administered to patients suffering from central nervous traumata as soon as possible at the place of accident, preferably in form of a preparation suitable for injection containing, for instance 5 to 100 mg of an active ingredient of formula I or an acid addition salt thereof. Subsequent treatment will ordinarily be carried out in a hospital by administering the medicament in the form of a intraveneous or intrathecal infusion or in form of an intravenous, intramuscular, subcutaneous or intraperitoneal injection.

Preparations suitable for infusions or injections are known per se and typically comprise, for instance, a bottle closed with a rubber stopper and containing the desired amount of the active compound or compounds in sterile, dry (lyophilized) form. A useful solution may be formed, for example, by adding a suitable solvent such as, for instance, sterile isotonic aqueous solutions of sodium chloride, glucose, inositol, mannitol or the like, in which the compounds of formula I are readily soluble. The resulting solution may be used as is for injections. Alternatively, by adjusting the resulting solution to the appropriate volume by adding it to the desired amount of the same solvent in an infusion flask, a solution which can be used for infusions is obtained.

Spray forms for intranasal or oral application of the compounds of formula I or for administration of these substances to the bronchia are also very useful. Such sprays can be prepared according to conventional techniques known in the art.

Oral or peroral application forms of the compounds of formula I may be used to maintain the plasma level resulting from the initial treatments with infusions or injection. Such application forms, e.g., tablets, dragees, capsules, granules, drops and syrups, are known per se. In their production conventionally used inorganic or organic adjuvants such as diluents, carriers, binders, lubricants, colors, flavorings, etc. may be added to the compounds of formula I.

For instance tablets or dragees, each containing 20 mg of a compound of formula I, may be prepared by mixing 20 g of the respective active ingredient of formula I together with 35 g of corn starch, 10 g of colloidial silica, 5 g of magnesium stearate, and, if desired, colors and/or flavorings. The blend is granulated, dried and compressed into 1,000 tables which may be subsequently film-coated or sugar-coated, if desired.

Capsules, each containing 20 mg of the compound formula I may be prepared for instance by mixing 20 g of the active ingredient with 376 g of lactose, granulating the mixture with an aqueous solution of 4 g gelatine, drying and finally filling into 1,000 hard-shell gelatine capsules.

Drops for intranasal application, which also may be used in the form of a spray, can be obtained in a manner known per se by dissolving the compound of formula I in an isotonic aqueous solution of sodium chloride mannitol, sorbitol, inositol or the like and adding an adhesive such as polyvinyl pyrrolidone or polyvinyl alcohol and/or a preservative such as 4-hydroxy-benzoic acid methyl ester or benzyl alcohol.

Suppositories containing an active ingredient corresponding to formula I may be prepared by melting 95 g of a commercially available suppository base at about 40 to 45° C., adding 3 g of salicylic or mandelic acid, followed by adding, while stirring, 2 g of the active ingredient and pouring the mixture into molds.

Compositions for percutaneous application of the compounds of formula I, such as plasters or the like containing a solution of the active ingredient, are also very convenient in many cases. Compositions of this type may optionally also contain a known membrane penetration enhancer, such as an N-alklyl lactam, etc.

The pharmaceutical compositions described above for peroral, rectal, percutaneous or intramuscular administration of the compounds of formula I preferably may be known types from which at least a portion of the active ingredient has a delayed release. Thus for a longer period of time, for instance 24 hours, a steady supply of the active ingredient to the patient can be achieved.

The manner in which the compounds of formula I are administered, the forms in which they are administered, and the amounts of the compounds of formula I to be administered to prevent or to treat injury after spinal cord or bran traumata all depend on the degree of the trauma or injury in the individual patient and will be determined individually by the physician in each case. In general, it is advisable to administer from about 1 to about 300 mg per day by infusion or by injection. Effective individual treatment doses may include, for instance, intravenous injections of 0.1 mg/kg, 0.2 mg/kg, 0.5 mg/kg and 1 mg/kg. Due to the known low toxicity of the compounds of formula I it is also possible to use still higher doses and/or to administer the desired amount of the compounds of formula I several times a day (e.g., 3 to 5 times daily) even for several consecutive days up to several weeks.

The surprising activity of the compounds of formula I and of medicaments containing these ingredients in the treatment of spinal cord injuries was demonstrated in the following, nonlimiting, animal experiment example:

EXAMPLE

Cats anesthetized with sodium pentobarbital were subjected under aseptic conditions to a laminectomy to expose the C-7 spinal segment. With the dura intact, the spinal cord was traumatized by dropping a 20 g weight a distance of 30 cm through a guide tube onto a 10 square-millimeter impact plate. Drugs were given intravenously as a bolus injection (0.5 ml) at 1 and 3 hours after injury. A group of 9 animals was treated with 0.2mg/kg of orotyl-L-histidyl-L-prolinamide dissolved in 0.5 ml of physiological saline. A second group of 7 animals was given 1 mg/kg L-pyro-2-aminoapidyl-L-nistidyl-thiazolidine-4-carboxamide (also dissolved in 0.5 ml of physiological saline), which compound is referred to hereinafter as "compound A" and which has been described in the literature as an active TRH-modification product and has also been compared with the aforementioned orotylL-histidyl-L-prolinamide (c.f. Metcalf in *Thyrotropin Releasing Hormone*, E. C. Griffiths et al., eds., Raven Press, New York, 1983, pp.

315-26). A control group of 11 animals was treated with 0.5 ml of physiological saline per animal.

Neurologic function was evaluated weekly for six weeks by a neurologist who was unaware of the treatment group and assessed according to a six-point ordinal scale as described by Faden et al. in *Neurology*, Vol. 33, pp. 673-678 (1983). Forelimb and hindlimb function were scored separately as follows: 0 = absence of voluntary movement; 1 = spontaneous movement but inability to support weight; 2 = ability to support weight but unable to walk; 3 = ability to walk but with marked spasticity and/or ataxia; 4 = ability to run but with mild spasticity or ataxia; and 5 = normal motor function. Forelimb and hindlimb scores were then added together to obtain a total functional score. Results of the experiment are shown in the following table;

| | Comparison of Neurologic Recovery in Cats After Traumatic Spinal Cord Injury | | |
|---|---|---|---|
| Weeks After Injury | Compound of Invention (n = 9) | Compound A (n = 7) | Saline Solution (n = 11) |
| 1 | 6 | 4 | 3 |
| 2 | 6 | 5 | 3 |
| 3 | 6 | 5 | 5 |
| 4 | 7 | 5 | 5 |
| 5 | 8 | 6 | 5 |
| 6 | 8 | 6 | 6 |

The test results demonstrate that after 6 weeks the neurologic and the motoric function in the animals treated with orotyl-L-histidyl-L-prolinamide were significantly improved, whereas the results achieved by compound A did not differ significantly from those of saline (although the dose of compound A administered was 5 times higher than that of crotyl-L-histidyl-L-prolinamide). These results also show that the activity of a TRH-modification product on the central nervous system (compound A has such an effect in a pronounced degree) has no relationship to the activity of that same product to prevent or cure posttraumatic nervous injuries (as demonstrated in the experiment described above in the model of paraplegia due to spinal cored injuries). In other words, the observed significant activity of crotyl-L-histidyl-L-prolinamide in this experiment could neither be expected nor predicted on the basis of the known other pharmacological properties of this compound of formula I.

The foregoing description and examples have been set forth merely to illustrate the invention and are not intended to be limiting. Since modifications of the described embodiments incorporating the spirit and substance of the invention may occur to persons skilled in the art, the scope of the invention should be limited solely with respect to the appended claims and equivalents.

We claim:

1. A method of preventing or treating posttraumatic nervous injuries comprising administering to a patient suffering from traumata of the spinal cord or of the brain an effective nervous injury affecting amount of a compound corresponding to the formula:

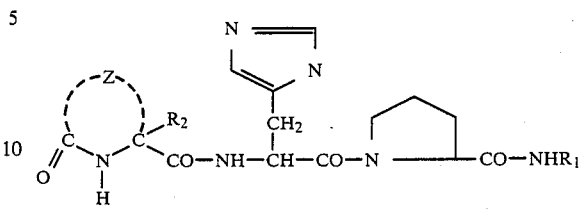

wherein $R_1$ represents a hydrogen atom, an alkyl group containing one to six carbon atoms, a cyclohexyl group or a benzyl group, Z is one of the following groups in which the valence marked with an asterisk is attached to the rink carbonyl group in formula I:

$$-NH-CO-\underset{R_4}{\overset{R_3}{\underset{|}{\overset{|}{C}}}}- \quad -\underset{R_6}{\overset{R_5}{\underset{|}{\overset{|}{C}}}}-S-CH_2-$$
$$\quad (a) \qquad\qquad (b)$$

If Z represents a group (a), $R_2$ and $R_3$ together represent an additional bond between the carbon atoms to which they are attached, or if Z represents a group (b), $R_2$ represents a hydrogen atoms, $R_4$ and $R_5$ are the same or different and each represents hydrogen or an alkyl group containing one to three carbon atoms, or $R_5$ also may represent a phenyl group, and $R_6$ represents hydrogen or a methyl group, in hydrated or unhydrated form or a pharmaceutically acceptable salt of such a compound with an acid.

2. A method according to claim 1 wherein said compound corresponds to the formula Ia:

Ia wherein $R_1$ is as defined in claim 1.

3. A method according to claim 1 wherein said compound corresponds to the formula Ib:

Ib wherein $R_1$ and $R_5$ are as defined in claim 1.

4. A method according to claim 1 wherein $R_1$ represents a hydrogen atom.

5. A method according to claim 2, wherein said compound of formula Ia is orotyl-L-histidyl-L-prolinamide in hydrated or unhydrated form.

6. A method according to claim 3, wherein said compound of formula Ib is 5-oxo-6-methyl-thiomorpholine-3(L)-carbonyl-L-histidyl-L-prolinamide in hydrated or unhydrated form.

7. A method according to claim 1, wherein the compound of formula I is administered parenterally.

8. A method according to claim 7, wherein the administration of the compound of formula I is by infusion.

9. A method according to claim 1, wherein the compound of formula I is administered percutaneously.

10. A method according to claim 1, wherein the compound of formula I is administered orally.

11. A method according to claim 1, wherein the compound of formula I is administered rectally.

12. A method according to claim 1, which comprises administering repeated periodic doses of the compound of formula I to obtain a long-lasting therapeutic effect.

* * * * *